US007129197B2

(12) United States Patent
Song et al.

(10) Patent No.: US 7,129,197 B2
(45) Date of Patent: Oct. 31, 2006

(54) SYNTHESIS OF POLY-ALPHA OLEFIN AND USE THEREOF

(75) Inventors: Wei Song, Houston, TX (US); William J. Heilman, Houston, TX (US)

(73) Assignee: Shell Oil Company, Houston, TX (US)

(*) Notice: Subject to any disclaimer, the term of this patent is extended or adjusted under 35 U.S.C. 154(b) by 98 days.

(21) Appl. No.: 10/230,482

(22) Filed: Aug. 29, 2002

(65) Prior Publication Data

US 2003/0055184 A1 Mar. 20, 2003

Related U.S. Application Data

(60) Provisional application No. 60/316,455, filed on Aug. 31, 2001.

(51) Int. Cl.
*C08F 4/44* (2006.01)
*C08F 110/14* (2006.01)
*C10M 143/08* (2006.01)

(52) U.S. Cl. ................ 508/591; 526/160; 526/348.2; 526/348.3; 526/348.5; 526/348.6; 526/943; 585/7; 585/10; 585/12; 585/255

(58) Field of Classification Search ............. 508/591; 585/255
See application file for complete search history.

(56) References Cited

U.S. PATENT DOCUMENTS

| | | | |
|---|---|---|---|
| 4,827,064 A | 5/1989 | Wu | |
| 4,990,709 A * | 2/1991 | Wu | 585/10 |
| 5,041,530 A * | 8/1991 | Van Doorn et al. | 528/392 |
| 5,044,438 A | 9/1991 | Young | 166/250 |
| 5,057,475 A | 10/1991 | Canich et al. | 502/104 |
| 5,064,802 A | 11/1991 | Stevens et al. | 502/155 |
| 5,068,476 A | 11/1991 | Wu et al. | |
| 5,087,788 A | 2/1992 | Wu | |
| 5,096,867 A | 3/1992 | Canich | 502/103 |
| 5,132,380 A | 7/1992 | Stevens et al. | 526/126 |
| 5,169,928 A * | 12/1992 | van Doorn et al. | 528/392 |
| 5,276,227 A * | 1/1994 | Wu et al. | 585/12 |
| 5,324,800 A | 6/1994 | Welborn, Jr. et al. | 526/160 |
| 5,688,887 A | 11/1997 | Bagheri et al. | |
| 5,703,187 A | 12/1997 | Timmers | 526/282 |
| 5,789,355 A | 8/1998 | Adams et al. | |
| 5,866,663 A | 2/1999 | Brookhart et al. | 526/170 |
| 5,880,241 A | 3/1999 | Brookhart et al. | 526/348 |
| 5,886,224 A | 3/1999 | Brookhart et al. | 564/272 |
| 5,891,963 A | 4/1999 | Brookhart et al. | 525/326.1 |

(Continued)

FOREIGN PATENT DOCUMENTS

EP 0 268214 A1 5/1988

(Continued)

OTHER PUBLICATIONS

V.M. Möhring et al., *Novel Polymerization of α-Olefins with the Catalyst System Nickel/Aminobis(imino)phosphorane*, Angew. Chem. Int. Ed. Engl., 1985, pp. 1001-1003, vol. 24, No. 11.

(Continued)

*Primary Examiner*—Ellen M. McAvoy

(57) ABSTRACT

One or more oligomers of an olefin are prepared in the presence of a single-site catalyst. Preferably, the olefin is an α-olefin, and the oligomers are a poly-alpha-olefin (PAO). The PAO so prepared is completely or substantially free of tertiary hydrogen resulting from isomerization. Consequently, the PAO possesses improved biodegradability, improved oxidation resistance, and/or a relatively higher viscosity index. The PAO has many useful applications, such as a component of a lubricant.

32 Claims, 3 Drawing Sheets

U.S. PATENT DOCUMENTS

| | | | | |
|---|---|---|---|---|
| 5,892,101 | A | 4/1999 | Brookhart et al. | 560/205 |
| 5,994,605 | A | 11/1999 | Bak et al. | |
| 6,015,767 | A | 1/2000 | Gibson et al. | 502/152 |
| 6,034,021 | A | 3/2000 | Wilson et al. | 502/103 |
| 6,034,259 | A | 3/2000 | Brookhart et al. | 556/137 |
| 6,060,437 | A | 5/2000 | Robson et al. | |
| 6,124,513 | A | 9/2000 | Heilman et al. | |
| 6,140,439 | A | 10/2000 | Brookhart et al. | 526/308 |
| 6,153,714 | A * | 11/2000 | Bansleben et al. | 526/348.1 |
| 6,203,923 | B1 * | 3/2001 | Bansleben et al. | 428/500 |
| 6,245,719 | B1 | 6/2001 | Kobori | 508/110 |
| 6,506,860 | B1 * | 1/2003 | Bansleben et al. | 526/171 |
| 6,703,356 | B1 * | 3/2004 | Wu | 508/591 |

FOREIGN PATENT DOCUMENTS

| | | |
|---|---|---|
| EP | 0468651 B1 | 9/1996 |
| EP | 0514828 B1 | 11/1997 |
| WO | 93/19104 | 9/1993 |
| WO | 95/00526 | 1/1995 |
| WO | WO 01/21675 A1 | 3/2001 |

OTHER PUBLICATIONS

F.C. Rix et al., *Energetics of Migratory Insertion Reactions in Pd(II) Acyl Ethylene, Alkyl Ethylene, and Alkyl Carbonyl Complexes*, J. Am. Chem. Soc., 1995, pp. 1137-1138, vol. 117.

G. Wilke, *Contributions to Organo-Nickel Chemistry*, Angew. Chem. Int. Ed. Engl., 1988, pp. 185-206, vol. 27.

Wahner et al., "*Oligomerisation of 1-pentene with metallocene catalysts*," Die Angewandte Makromolekulare Chemie, 1999, pp. 49-55, vol. 270, No. 4686.

Grumel et al., "*Homopolymerization of Higher 1-Olefins with Metallocene/MAO Catalysts,*" Macromol. Mater. Eng., 2001, pp. 480-487, vol. 286.

International Search Report, Jan. 31, 2003.

* cited by examiner

SYNTHESIS OF POLY-ALPHA OLEFIN AND USE THEREOF

PRIOR RELATED APPLICATIONS

This application claims priority to a prior U.S. Provisional patent application Ser. No. 60/316,455, filed Aug. 31, 2001, entitled Synthesis of Poly-Alpha Olefin and Use Thereof, which is incorporated by reference in its entirety.

FEDERALLY SPONSORED RESEARCH STATEMENT

Not applicable.

REFERENCE TO MICROFICHE APPENDIX

Not applicable.

FIELD OF THE INVENTION

This invention relates to poly-alpha olefin oligomers and methods of making such oligomers. More particularly, the invention relates to a composition for a lubricant and methods of making the composition.

BACKGROUND OF THE INVENTION

Synthetic hydrocarbons have been used as lubricant components for automotive, aviation, and industrial applications. In the automotive industry, lubricant oils include engine oils, brake fluids, and lubricating greases. Engine oils for an automobile include 2-stroke oils, 4-stroke oils, and gear oils. In the aviation industry, lubricant oils include turbine oils, piston engine oils, hydraulic fluids, and lubricating greases. In industrial applications, lubricant oils are used as gas-turbine oils, gear oils, bearing and circulation oils, compressor oils, hydraulic oils, metal-working fluids, heat-transfer and insulation oils, and lubricating greases.

Poly-$\alpha$-olefins (PAOs; polyalphaolefins) are synthetic hydrocarbons which have been used as lubricant base oils. PAOs have good flow properties at low temperatures, relatively high thermal and oxidative stability, low evaporation losses at high temperatures, higher viscosity index, good friction behavior, good hydrolytical stability, and good erosion resistance. PAOs are not toxic and are miscible with mineral oils and esters. Consequently, PAOs are suited for use in engine oils, compressor oils, hydraulic oils, gear oils, and greases. However, PAOs that have been characterized to date, have limited oxidative stability, limited biodegradability and limited additive miscibility. Therefore, it may not be suitable for use as high-performance gear oils and fast biodegradable oils. Structurally, PAOs often include tertiary hydrogen which is prone to oxidation. Therefore, it would be desirable to minimize the presence of tertiary hydrogen so as to improve oxidation resistance of synthetic hydrocarbons.

Currently, PAOs are synthesized by a two-step reaction sequence from linear $\alpha$-olefins, which are derived from ethylene. The first step is the synthesis of a mixture of oligomers, which are polymers of relatively low molecular weight. This first step is catalyzed using a boron trifluoride catalyst in conjunction with a protic catalyst such as water, alcohol, or a weak carboxylic acid. However, it has been observed that boron trifluoride catalysis causes excess skeletal branching during the oligomerization process. An increase in the amount of skeletal branching directly correlates with an increase in the number of tertiary hydrogens in the molecule, which are prone to oxidation, and therefore exhibit poor stability when used in lubricants. The second step in the manufacturing process entails hydrogenation of the unsaturated oligomer.

Due to the increasing demand for product performance, there is a need for a relatively more stable PAO and a lubricant made therefrom. A PAO made in a process in which no substantially additional tertiary hydrogens are introduced during oligomerization, would be less prone to oxidation, and would possess greater stability than the branched PAOs currently known in the art. This type of PAO is hereafter referred to as a non-isomerized oligomer.

SUMMARY OF THE INVENTION

In an embodiment of the invention, non-isomerized oligomers are provided, which comprise repeating units of olefin monomers organized in a substantially head to tail molecular structure, wherein the oligomer has a molecular weight of about 10,000 or less, and is prepared in the presence of a single site catalyst.

In an embodiment of the invention, the olefin monomer is selected from a group consisting of aliphatic olefins, aromatic olefins, and cyclic olefins. The aliphatic olefin of the present invention may be an $\alpha$-olefin.

In an embodiment of the invention, the oligomer is substantially free of tertiary hydrogen formed due to isomerization, i.e., a hydrogen which is attached to a carbon that is directly attached to three carbons.

In an embodiment of the invention, the oligomer displays improved oxidative stability and biodegradibility.

In a further embodiment, the oligomer is hydrogenated by reaction with hydrogen gas in the presence of a catalytic amount (0.1 to 5 wt. %) of a hydrogenation catalyst.

In an embodiment of the invention, the oligomer may be a dimer, a trimer, a tetramer, a pentamer, a higher oligomer, or a mixture thereof.

In an embodiment of the invention, the unsaturation, such as the double bonds of the oligomer, may be functionalized by the addition of a moiety containing polar groups, ester groups, polyether groups, detergents, and the like.

The polyalphaolefins obtained in accordance with embodiments of the invention may be hydrogenated to formulate lubricant oils in amounts from about 0.1 wt % to about 99 wt %. The lubricant oils may also contain a number of conventional additives in amounts required to provide various functions.

BRIEF DESCRIPTION OF THE DRAWINGS

In order to assist in the understanding of the invention, reference is now made to the appended drawings. The drawings are intended to be exemplary only, and should not be construed as limiting the invention

DESCRIPTION OF EMBODIMENTS OF THE INVENTION

Figure 1:
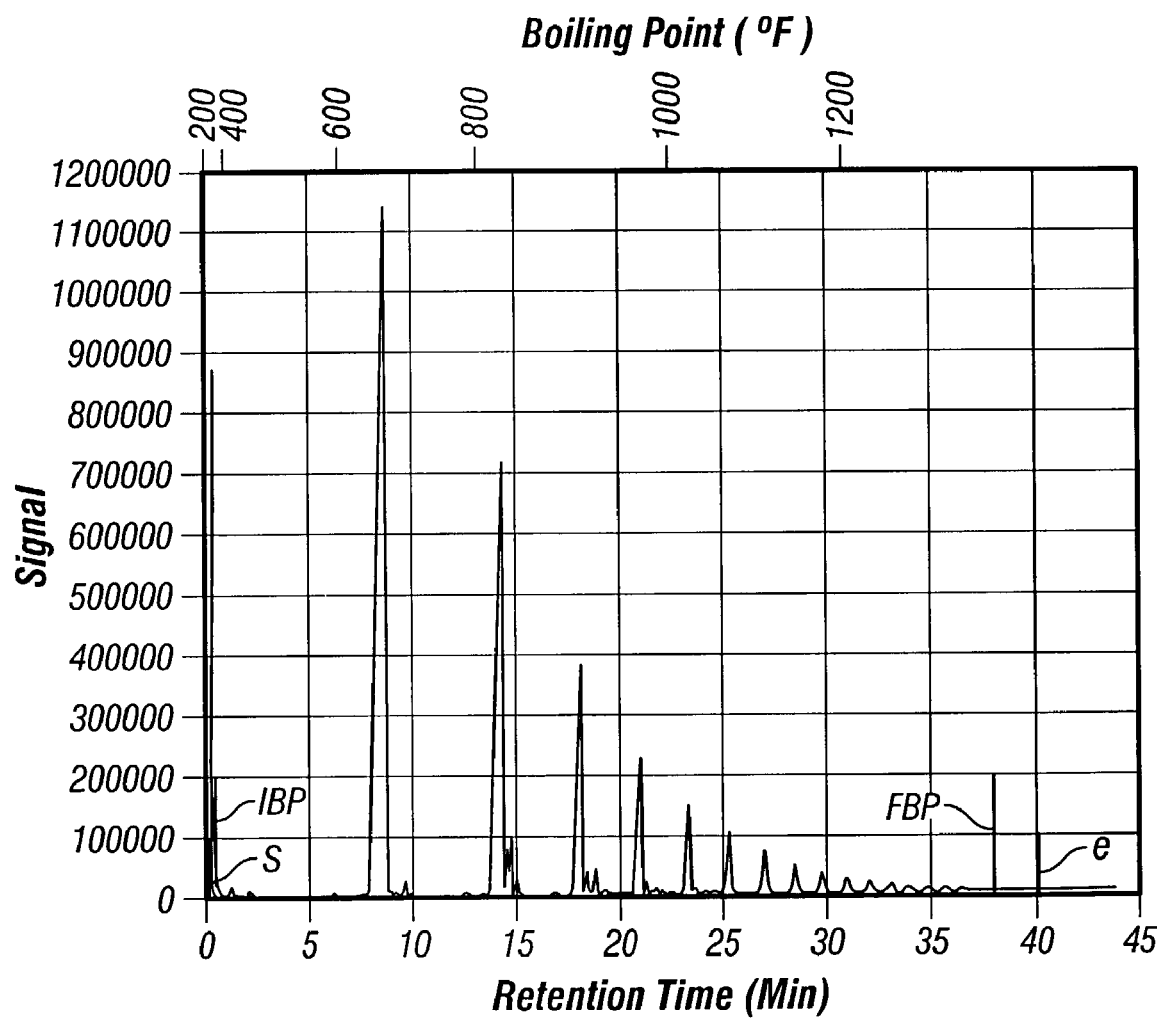
FIG. 1 shows a high temperature simulated distillation chromatogram for the reaction product described in Example 8.

In the following description, all numbers disclosed herein are approximate values, regardless whether the word "about" or "approximate" is used in connection therewith. They may vary by up to 1%, 2%, 5%, or, sometimes, 10 to 20%. Whenever a numerical range with a lower limit, $R^L$ and an upper limit, $R_U$, is disclosed, any number R falling within the range is specifically disclosed: $R=R^L+k*(R^U-R^L)$, wherein k is a variable ranging from 1% to 100% with a 1% increment, i.e., k is 1%, 2%, 3%, 4%, 5%, . . . ,50%, 51%, 52%, . . . ,95%, 96%, 97%, 97%, 98%, 99%, to 100%. Moreover, any numerical range defined by two R numbers as defined in the above is also specifically disclosed.

Embodiments of the invention provide non-isomerized oligomers comprising repeating units of olefin monomers organized in a substantially head to tail molecular structure, wherein the oligomer has a molecular weight of about 10,000 or less, and is prepared in the presence of a single site catalyst. The molecular weight of the oligomer may range from a molecular weight of about 3,000 or less to about 10,000 or less. The molecular weight of the oligomer may preferably be about 9,000 or less, about 7,000 or less, or about 5,000 or less.

The term "regio-regular" as used herein, refers to an oligomer comprising repeating units of olefin monomers organized in a head to tail molecular structure. The oligomers described herein are substantially regio-regular, i.e., substantially free of head-to-head and tail-to-tail configurations. In certain embodiments of the invention, the oligomers display ≧60% regio-regularity. In other embodiments of the invention, the oligomers display ≧70% regio-regularity. Certain embodiments of the invention display ≧80% regio-regularity. Preferred embodiments of the invention display ≧90% regio-regularity. In certain embodiments of the invention, the oligomers are characterized by a regio-regularity of about 95–100%. The regio-regularity of the oligomers can be measured by nuclear magnetic resonance spectroscopy.

The term "poly-α-olefin" used herein refers to hydrocarbons manufactured by the oligomerization of α-olefins. Generally, suitable a-olefins are represented by the following formula:

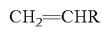

where R can be any hydrocarbyl group, such as alkyl, aryl, or aralkyl. Some specific examples of preferred α-olefins include, but are not limited to, 1-propene (propylene), 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene, 1-eicosene, 4-methyl-1-pentene, 5-methyl-1-nonene, 3-methyl-1-pentene, 3,5,5-trimethyl-1-hexene and vinylcyclohexene. Styrene and p-methylstyrene are preferred styrenic olefins. Another preferred class of α-olefins is linear α-olefins. Typically, monomers of the same type are used in oligomerization reactions, although a mixture of two or more kinds of monomers may also be used, if desired.

The term "single site" catalyst used herein refers to those catalysts which have only one catalytic site for each catalyst molecule. This is in contrast to the traditional Ziegler-Natta catalyst which has multiple catalytic sites per catalyst molecule for olefin polymerization. One class of single site catalysts is metallocene catalysts. Another class of single site catalysts is constrained geometry catalysts. Constrained geometry catalysts are disclosed in U.S. Pat. Nos. 5,064,802, 5,132,380, 5,703,187, 6,034,021, EP 0 468 651, EP 0 514 828, WO 93/19104, and WO 95/00526, all of which are incorporated by references herein in their entirety. Metallocene catalysts are disclosed in U.S. Pat. Nos. 5,044,438; 5,057,475; 5,096,867; and 5,324,800, all of which are incorporated by reference herein in their entirety. It is noted that constrained geometry catalysts may be considered as metallocene catalysts, and both are sometimes referred to in the art as single-site catalysts. Such catalyst systems comprise preferably the combination of (a) metallocene compounds which are compounds of a transition metal of Group IVb of the Periodic Table and (b) an aluminoxane. Other single site catalysts are disclosed, for example, in U.S. Pat. Nos. 5,866,663; 5,880,241; 5,886,224; 5,891,963; 5,892,101; 6,034,259; 6,140,439; and 6,015,767. The disclosures of all of the preceding patents are incorporated by reference herein in their entirety.

In an embodiment of the invention, the olefin monomer may be selected from aliphatic olefins, aromatic olefins, or cyclic olefins. The aliphatic olefin may be an α-olefin. Suitable α-olefins may include, but are not limited to, propylene, 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene or 1-eicosene. In an aspect of the invention, the oligomer is synthesized using a single species of olefin monomer. In another aspect of the invention, the oligomer is synthesized using one or more different species of olefin monomer.

In an embodiment of the invention, the oligomer is substantially free of tertiary hydrogen formed due to isomerization, i.e., a hydrogen which is attached to a carbon that is directly attached to three carbons. An oligomer substantially free of tertiary hydrogens added as a result of the oligomerization process is referred to as a non-isomerized oligomer herein. In some embodiments of the invention, the oligomer is completely free of tertiary hydrogen resulting from isomerization. The term "non-isomerized oligomer" does not preclude oligomers made in a process in which isomerization occurs to some limited extent. Preferably, no isomerization occurs during oligomerization. As such, the PAO preferably is characterized by a uniform, head-to-tail structure, improved biodegradability, higher viscosity index and/or better oxidative stability.

In an embodiment of the invention, the number of tertiary hydrogens not including those due to isomerization is calculated using the following formulae. Isomerization during the oligomerization reaction would render the number of the total tertiary hydrogen higher than that calculated by the formulae. Therefore, the term "substantially free of tertiary hydrogen due to isomerization" means that the number of tertiary hydrogen is equal to or substantially equal to that calculated by the following formulae.

In the absence of hydrogen in the oligomerization reaction, the number of tertiary hydrogens (t-H) in the oligomers is:

$$TH=A*N+(N-1)$$

where TH is total number of t-H in the oligomer, A is the number of t-H in the monomer and N is the number of repeating units in the oligomer. Therefore, in a dimer N=2; in a trimer N=3, and so on. For example, if the monomer is decene ($C_{10}H_{20}$), A=0; TH in a dimer is 1; in a trimer is 2; in a tetramer is 3, and so on. If the monomer is 4-methyl-1-pentene, A=1; TH in a dimer is 3; in a trimer is 5; in a tetramer is 7, and so on.

Using decene oligomers as an illustrative example: Bis(cyclopentadienyl)zirconium dichloride/methylaluminoxane (Cp$_2$ZrCl$_2$/MAO) catalyst system is used to oligomerize decene. MAO reacts with Cp$_2$ZrCl$_2$ to form the Cp$_2$Zr$^+$CH$_3$ active species. Cp$_2$Zr$^+$CH$_3$ initiates insertion of decene monomer in between Zr$^+$ and CH$_3$ leading to the formation of the following species:

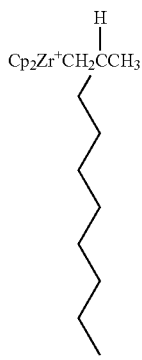

The CH$_3$ stays at the end of the chain regardless of the insertions of more monomers. After a second insertion of decene monomer, it becomes

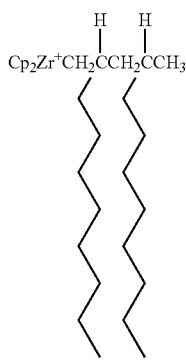

β-elimination of H to terminate chain growth results in the formation of the double bond on one end of the oligomer chain. Therefore, following chain termination, a decene dimer will have the following structure (before hydrogenation):

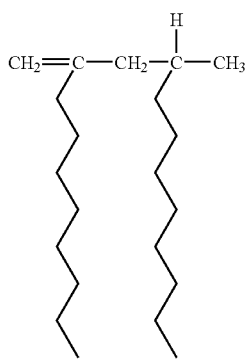

The dimer has one t-H.

A decene trimer has a structure like:

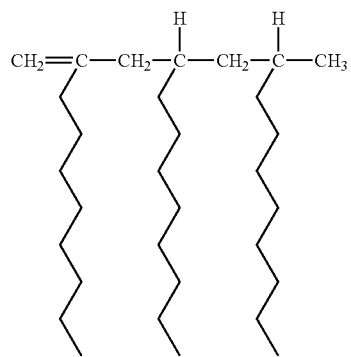

The trimer has two t-H's.

When a monomer itself contains t-H's, such as in 4-methyl-1-pentene, TH should be the sum of A*N (contribution of t-H's in the side chain of the oligomer) and N−1.

When an additional hydrogenation step is applied to the oligomer, the double bond at the chain end becomes saturated and the structure of a dimer becomes

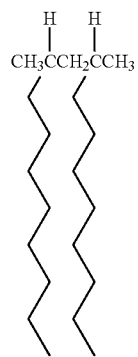

and the formula for hydrogenated oligomer becomes:

TH=A*N+N

When hydrogen is used during the oligomerization reaction, the formula is:

TH=A*N+N

In the presence of hydrogen in the oligomerization step, most of the oligomer products are saturated even before an additional hydrogenation step is applied to process the oligomers. β-elimination becomes much less significant. Therefore, a dimer formed under this condition has the following structure:

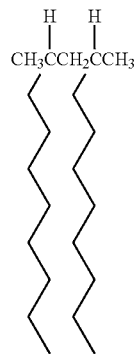

The dimer has two t-H's.

The trimer has a structure like:

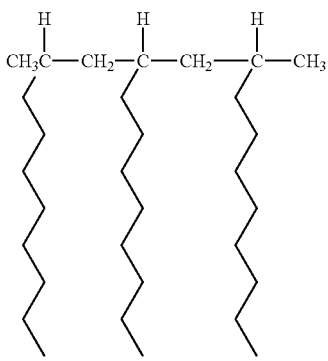

The trimer has three t-H's.

In an embodiment of the invention, the oligomer displays improved oxidative stability and biodegradibility.

In a further embodiment, the oligomer is hydrogenated by reaction with hydrogen gas in the presence of a catalytic amount (0.1 to 5 wt. %) of a hydrogenation catalyst. Examples of suitable hydrogenation catalysts are metals of Group VIII of the Periodic Table such as iron, cobalt, nickel, rhodium, palladium and platinum. These catalysts may be deposited on alumina, on silica gel, or on activated carbon in preferred embodiments. Of these catalysts, palladium and nickel are preferred. Palladium on activated carbon and nickel on kieselguhr are especially preferred. In an embodiment of the invention, the synthesized oligomer has some unsaturation. The unsaturation is primarily in the form of vinylidene groups. In another embodiment of the invention the synthesized oligomer is saturated. In an aspect of the invention, the oligomer is synthesized as an unsaturated oligomer, and it is subsequently hydrogenated to produce a saturated oligomer.

In an embodiment of the invention, the oligomer may be a dimer, a trimer, a tetramer, a pentamer, a higher oligomer, or a mixture thereof. In an aspect of the invention, the oligomer may comprise "TH" tertiary hydrogens (in the absence of hydrogen in the oligomerization reaction), where TH=A times N+(N−1) where TH is total number of tertiary hydrogens in the oligomer, A is the number of tertiary hydrogens in the monomer and N is the number of repeating units in the oligomer. In the presence of hydrogen, the number of tertiary hydrogens in the oligomer is calculated as TH=A times N+N.

In an embodiment of the invention, the unsaturation, such as the double bonds of the oligomer, may be functionalized by the addition of a moiety containing polar groups, ester groups, polyether groups, detergents, and the like. More specifically, preferred functional compounds include vinyl fluoride, vinyl chloride, vinyl bromide, vinyl iodide, vinyl acetate, acrylate esters of $C_1$–$C_{20}$ alcohols, vinyl ketones, vinyl amines, vinyl amides, acrylonitrile, acrylamide, vinyl oxazoles, vinyl thiazoles, and vinyl ethers. More preferred monomers include vinyl chloride, vinylidene chloride, vinyl bromide, vinyl iodide, vinyl acetate, methyl acrylate methyl vinyl ether and isobutyl vinyl ether. In an embodiment of the invention, compounds containing one or more functional groups, such as hydroxy, carboxylic acid, amine, carboxylic ester, phenolic ester, carboxylic amide, phosphate, sulfonamide, and thiophosphate may also be used. Any known or unknown chemistry capable of functionalizing an unsaturated moiety may be employed to functionalize an unsaturated oligomer.

Embodiments of the invention also provide a poly-alpha-olefin composition comprising one or more oligomers of an alpha-olefin, the oligomers having a molecular weight of about 10,000 or less and characterized by being substantially free of tertiary hydrogen resulting from isomerization. The PAOs obtained in accordance with embodiments of the invention may be hydrogenated to formulate lubricant oils in amounts from about 0.1 wt % to about 99 wt %. The lubricant oils may also contain a number of conventional additives in amounts required to provide various functions. These additives include, but are not limited to, ashless dispersants, metal or overbased metal detergent additives, anti-wear additives, viscosity index improvers, antioxidants, rust inhibitors, pour point depressants, friction reducing additives, and the like.

Suitable ashless dispersants may include, but are not limited to, polyalkenyl or borated polyalkenyl succinimide where the alkenyl group is derived from a $C_3$–$C_4$ olefin, especially polyisobutenyl having a number average molecular weight of about 5,000 to 7,090. Other well known dispersants include the oil soluble polyol esters of hydrocarbon substituted succinic anhydride, e.g. polyisobutenyl succinic anhydride, and the oil soluble oxazoline and lactone oxazoline dispersants derived from hydrocarbon substituted succinic anhydride and di-substituted amino alcohols. Lubricating oils typically contain about 0.5 to about 5 wt % of ashless dispersant.

Suitable metal detergent additives are known in the art and may include one or more of overbased oil-soluble calcium, magnesium and barium phenates, sulfurized phenates, and sulfonates (especially the sulfonates of $C_{16}$–$C_{50}$ alkyl substituted benzene or toluene sulfonic acids which have a total base number of about 80 to 300). These overbased materials may be used as the sole metal detergent additive or in combination with the same additives in the neutral form; but the overall metal detergent additive should have a basicity as represented by the foregoing total base number. Preferably they are present in amounts of from about 3 to 6 wt % with a mixture of overbased magnesium sulfurized phenate and neutral calcium sulfurized phenate (obtained from $C_9$ or $C_{12}$ alkyl phenols).

Suitable anti-wear additives include, but are not limited to, oil-soluble zinc dihydrocarbyldithiophosphates with a total of at least 5 carbon atoms and are typically used in amounts of about 1–6% by weight.

Suitable viscosity index improvers, or viscosity modifiers, include, but are not limited to olefin polymers, such as polybutene, hydrogenated polymers and copolymers and terpolymers of styrene with isoprene and/or butadiene, polymers of alkyl acrylates or alkyl methacrylates, copolymers of alkyl methacrylates with N-vinyl pyrrolidone or dimethylaminoalkyl methacrylate, post-grafted polymers of ethylene and propylene with an active monomer such as maleic anhydride which may be further reacted with alcohol or an alkylene polyamine, styrene-maleic anhydride polymers post-reacted with alcohols and amines and the like. These are used as required to provide the viscosity range desired in the finished oil in accordance with known formulating techniques.

Examples of suitable oxidation inhibitors include, but are not limited to hindered phenols, such as 2,6-di-tertiary-butyl-paracresol, amines sulfurized phenols and alkyl phenothiazones. Usually, a lubricating oil may contain about 0.01 to 3 wt % of oxidation inhibitor, depending on its effectiveness. For improved oxidation resistance and odor control, it has been observed that up to about 5 wt. % of an antioxidant should be included in the aforementioned formula. One suitable example of such, butylated hydroxytoluene ("BHT"), or di-t-butyl-p-cresol, is sold by many suppliers including Rhein Chemie and PMC Specialties. Another suitable example is Irganox L-64 from Ciba Gigy Corp.

Rust inhibitors may be employed in very small proportions such as about 0.1 to 1 weight percent with suitable rust inhibitors being exemplified by $C_9$–$C_{30}$ aliphatic succinic acids or anhydrides such as dodecenyl succinic anhydride. Antifoam agents are typically include, but are not limited to polysiloxane silicone polymers present in amounts of about 0.01 to 1 wt %.

Pour point depressants are used generally in amounts of from about 0.01 to about 10.0 wt %, more typically from about 0.1 to about 1 wt %, for most mineral oil basestocks of lubricating viscosity. Illustrative of pour point depressants which are normally used in lubricating oil compositions include, but are not limited to, polymers and copolymers of n-alkyl methacrylate and n-alkyl acrylates, copolymers of di-n-alkyl fumarate and vinyl acetate, alpha-olefin copolymers, alkylated naphthalenes, copolymers or terpolymers of alpha-olefins and styrene and/or alkyl styrene, styrene dialkyl maleic copolymers and the like.

As discussed in U.S. Pat. No. 6,245,719, which is fully incorporated by reference herein, a variety of additives may be used to improve oxidation stability and serviceability of lubricants used in automotive, aviation, and industrial applications. These additives include calcium phenate, magnesium sulfonate and alkenyl succinimide to agglomerate solid impurities, a combination of an ashless dispersant, metallic detergent and the like, an oxidation inhibitor of sulfur-containing phenol derivative or the like, an oxidation inhibitor or the like, or mixtures thereof.

In addition to the foregoing, another embodiment of the invention provides a method of making a non-isomerized oligomer which comprises: contacting repeating units of an olefin monomer in the presence of a single site catalyst; and effecting oligomerization of the olefin monomer to produce a non-isomerized oligomer organized in a substantially head to tail molecular structure, with a molecular weight of about 10,000 or less. The molecular weight of the oligomer may range from a molecular weight of about 3,000 or less to about 10,000 or less. The molecular weight of the oligomer may preferably be about 9,000 or less, about 7,000 or less, or about 5,000 or less. The method involves the oligomerization of olefin monomers which involves relatively low to no isomerization, thereby resulting in relatively fewer branches (i.e.) tertiary hydrogensin the product molecule. The molecular weight of the oligomer may be controlled by modulating the temperature of the synthesis, the concentration of the catalyst, or through the use of hydrogen in the synthesis.

Any catalyst which is capable of effecting oligomerization of the olefin monomer may be used in embodiments of the invention. Preferably, a selected catalyst is capable of minimizing the occurrence of isomerization of an olefin monomer (e.g. an α-olefin) during the reaction. Suitable catalysts include, but are not limited to, single-site catalysts (both metallocene catalysts and constrained geometry catalysts), and variations therefrom. They include any known and presently unknown catalysts for olefin polymerization. It should be understood that the term "catalyst" as used herein refers to a metal-containing compound which is used, along with an activating cocatalyst, to form a catalyst system. The catalyst, as used herein, is usually catalytically inactive in the absence of a cocatalyst or other activating technique. However, not all suitable catalyst are catalytically inactive without a cocatalyst and thus requires activation.

As mentioned above, suitable catalyst systems may comprise preferably the combination of (a) metallocene compounds which are compounds of a transition metal of Group IVb of the Periodic Table and (b) an aluminoxane. Such metallocene compounds are preferably tri- and tetravalent metals having one or two hapto $\eta^5$-ligands selected from the group comprising cyclopentadienyl, indenyl, fluorenyl with the maximum number of hydrogen substituted with alkyl, alkenyl, aryl, allylaryl, arylalkyl or benzo radicals to none. When there are two $\eta^5$-ligands, they may be the same or different which are either connected by bridging groups, selected from the group comprising, $C_1$–$C_4$ alkylene, $R_2Si$, $R_4Si_2$, $R_2Si$—O—Si—$R_2$, $R_2Ge$, $R_2P$, $R_2N$ with R being hydrogen, alkyl or aryl radicals, or the two $\eta^5$-ligands are not connected. The non-hapto ligands are either halogen or R, there are two or one such ligands for the tetravalency or trivalency transition metal, respectively.

Where there is only one hapto $\eta^5$-ligands, it can be selected from the group comprising cyclopentadienyl, indenyl, fluorenyl with from the maximum number of hydrogen substituted with R or benzo radicals or to none. The transition metal will have three or two non-hapto ligands in the +4 and +3 oxidation state, respectively. One hydrogen of the hapto ligand may be substituted with a heteroatom moiety selected from the group NR, $NR_2$, PR, $PR_2$ which are connected by $C_1$–$C_4$ alklene, $R_2Si$, $R_4Si_2$ to the $\eta^5$-ring. The appropriate number of non-hapto ligands is three for tetravalent metal in the case of coordinate bonding $NR_2$ or $PR_2$ moiety and one less non-hapto ligands for the trivalent metal. These numbers are decreased by one in the case of covalent bonding NR or PR moieties.

Illustrative but not limiting examples of titanium compounds comprise bis(cyclopentadienyl)dimethyltitanium, bis(cyclopentadienyl)diisopropyltitanium, bis(cyclopentadienyl)methyltitanium monochloride, bis(cyclopentadienyl)ethyltitanium monochloride, bis(cyclopentadienyl)isopropyltitanium monochloride, bis(cyclopentadienyl)titanium dichloride, dimethylsilylene (1-$\eta^5$-2,3,4,5-tetramethylpentadienyl)(t-butylamido)titanium dichloride, 2-dimethyl aminoethyl-$\eta^5$-cyclopentadienyl titanium dichloride.

Illustrative but not limiting examples of zirconium compounds comprise as bis(isopropylcyclopentadienyl)zirconium dichloride, bis(cyclopentadienyl)dimethyl-zirconium, bis(cyclopentadienyl)diethylzirconium, bis(methylcyclopentadienyl)diisopropylzirconium, bis(cyclopentadienyl)m-ethylzirconium monochloride, bis-(cyclopentadienyl)ethylzirconium monochloride, bis(cyclopentadienyl)dimethyl zirconium, rac-ethylene bis(1-$\eta^5$-indenyl)zirconium dichloride, rac-ethylene bis(1-$\eta^5$-indenyl)dimethyl zirconium, rac-ethylene bis(1-$\eta^5$-4,5,6,7 tetrahydroindenyl)zirconium dichloride and isopropylidene-(1-$\eta^5$-cyclopentadienyl)(9-$\eta^5$-fluoronyl)zirconium dichloride.

Illustrative but not limiting examples of hafnium compounds comprise bis(cyclopentadienyl)dimethylhafnium, bis(cyclopentadienyl)methylhafnium monochloride, bis(cyclopentadienyl)hafnium dichloride, and rac-ethylene bis(1-$\eta^5$-indenyl)hafnium dichloride.

The aluminoxane co-catalyst useful in the catalysts of the present invention are polymeric aluminum compounds which can be represented by the general formulae (R—Al—O)$_n$ which is a cyclic compound and R(R—Al—O—)$_n$AlR$_2$, which is a linear compound. In the general formula R is a $C_1$–$C_5$ alkyl group such as, for example, methyl, ethyl, propyl, butyl and pentyl and n is an integer from 1 to about 20. Most preferably, R is methyl and n is about 4. Generally, in the preparation of aluminoxanes from, for example, aluminum trimethyl and water, a mixture of the linear and cyclic compounds is obtained.

The proportion of the catalyst comprising a compound of a transition metal of Group IVb of the Periodic Table may be, for example, $10^{-8}$ to 1 mole/liter, preferably $10^{-3}$ to $10^{-2}$ mole/liter, as the concentration of the catalyst comprising a compound of a transition metal in the oligomerization reaction. The proportion of the aluminoxane used may be, for example, $10^{-4}$ to 10 mole/liter, preferably $10^{-3}$ to $5 \times 10^{-1}$ mole/liter, as the concentration of the aluminum atom in the oligomerization reaction. The ratio of the aluminum atom to the transition metal in the oligomerization reaction system may be, for example, in the range of 25 to $10^6$, preferably 50 to $10^4$. The molecular weight of the oligomer may be controlled by using hydrogen, and/or by adjusting the oligomerization temperature, or by changing the monomer and catalyst concentrations.

While the above description represents preferred catalysts for use in the invention, equivalent catalysts and combinations may also be used to effect the olefin oligomerization.

The oligomerization reaction in an embodiment of the invention may be carried out in absence of a solvent or in a hydrocarbon solvent. Examples of a hydrocarbon solvent suitable for this purpose are aliphatic hydrocarbons such as butane, isobutane, pentane, hexane, octane, decane, dodecane, hexadecene and octadecane; alicyclic hydrocarbons such as cyclopentane, methylcyclopentane, cyclohexane and cyclooctane; aromatic hydrocarbons such as benzene, toluene and xylene; and petroleum fractions such a gasoline, kerosene, lubricant base stocks and light oils. The starting olefins or PAOs may themselves serve as the hydrocarbon medium. Among these hydrocarbon media, the aromatic hydrocarbons and the starting olefins may be preferably used in the process of this invention.

The oligomerization temperature in this first step of the process of the invention may range, for example, from about 0° C. to about 200° C., preferably from about 20° C. to about 120° C. In a preferred embodiment of the invention, the single-site catalyst used is a metallocene-based catalyst comprising bis(cyclopentadienyl)zirconium dichloride.

As mentioned above, oligomers according to embodiments of the invention may have some level of unsaturation, such as the presence of double bonds. The unsaturated bonds may be hydrogenated in a hydrogenation reaction. The hydrogenation reaction can be carried out in the presence or absence of solvents. Solvents are necessary only to increase the volume. Examples of suitable solvents are hydrocarbons such as pentane, hexane, heptane, octane, decane, cyclohexane, methycyclohexane and cyclooctane aromatic hydrocarbons such as toluene, xylene or benzene. The temperature of the hydrogenation reaction may range, for example, from about 150° C. to about 500° C., preferably from about 250° C. to about 350° C. The hydrogenation reaction pressure may be, for example, in the range of 250–1000 psig hydrogen. The hydrogenated oligomeric product is then recovered by conventional procedures. In the hydrogenated product, the double bonds formed in the oligomerization step have been hydrogenated so that the oligomer is a separate type of product. The hydrogenated oligomer may be used in the same manner as the unhydrogenated oligomer.

The working examples provided below are intended to merely exemplify the invention without limiting its scope.

EXAMPLE 1

A 120 ml pressure reaction bottle with a magnetic stir bar was thoroughly evacuated followed by purging with argon. Then the bottle was charged with 10 ml of dried toluene (distilled over potassium) and 10 ml of 1-tetradecene (dried over 5A molecular sieves). At 40° C., 4 ml of 3.3 M methylaluminoxane in toluene solution was added to the reaction bottle and stirred for 15 minutes. Then 4 ml of $6.2 \times 10^{-3}$ M bis(cyclopentadienyl)zirconium dichloride in toluene solution was injected into the bottle to start the reaction. Temperature of the reaction system was controlled by a constant temperature bath within ±1° C. range. After 1 hour, 50 ml of 10% HCl aqueous solution was added to the bottle to quench the reaction and the resulting mixture was stirred for two hours. The organic layer was then isolated and further washed twice with 50 ml of deionized water. Toluene solvent was subsequently removed from the organic layer on a rota-evaporator. Analysis of the product mixture by high temperature simulated distillation (ASTM D2887, Modified) indicated oligomers yield was 66%. The oligomers contained about 42% dimer, 26% trimer, 15% tetramer, 8% pentamer and 9% higher oligomers.

EXAMPLE 2

The procedure was essentially the same as Example 1, except the reaction was run at 60° C. The oligomers yield was 86%. The oligomers contained about 60% dimer, 23% trimer, 8% tetramer, 4% pentamer and 5% higher oligomers.

EXAMPLE 3

The procedure was essentially the same as Example 1, except the reaction was run at 60° C. and 2 ml of 3.3 M methylaluminoxane in toluene solution was used. The oligomers yield was 87%. The oligomers contained about 68% dimer, 20% trimer, 7% tetramer, 3% pentamer and 2% higher oligomers.

EXAMPLE 4

The procedure was essentially the same as Example 1, except the reaction was run at 70° C. and 2 ml of 3.3 M methylaluminoxane in toluene solution was used. The oligomers yield was 89%. The oligomers contained about 71% dimer, 19% trimer, 7% tetramer, 1% pentamer and 2% higher oligomers.

EXAMPLE 5

The procedure was essentially the same as Example 1, except the reaction was run at 70° C. and 1 ml of 3.3 M methylaluminoxane in toluene solution was used. The oligomers yield was 88%. The oligomers contained about 78% dimer, 15% trimer, 5% tetramer, 1% pentamer and 1% higher oligomers.

EXAMPLE 6

The procedure was essentially the same as Example 1, except the starting monomer was 1-decene instead of 1-tetradecene, and the reaction was run at 60° C. with 2 ml of 3.3 M methylaluminoxane in toluene solution was used. The oligomers yield was 94%. The oligomers contained about 60% dimer, 23% trimer, 9% tetramer, 3% pentamer and 5% higher oligomers.

EXAMPLE 7

The procedure was essentially the same as Example 1, except the starting monomer was 1-decene instead of 1-tetradecene, and the reaction was run at 60° C. with 1 ml of 3.3 M methylaluminoxane in toluene solution was used. The oligomers yield was 95%. The oligomers contained about 71% dimer, 19% trimer, 6% tetramer, 2% pentamer and 2% higher oligomers.

EXAMPLE 8

A 500 ml pressure reaction bottle with a magnetic stir bar was thoroughly vacuumed followed by purging with argon. Then the bottle was charged with 50 ml of dried toluene (distilled over potassium) and 100 ml of 1-decene (dried over 5A molecular sieves). At 50° C., 20 ml of 3.3 M methylaluminoxane in toluene solution was added to the reaction bottle and stirred for 20 minutes. Then 4 ml of 0.049 M bis(isopropylcyclopentadienyl)zirconium dichloride in toluene solution was injected into the bottle to start the reaction. Temperature of the reaction system was controlled by a constant temperature bath within ±1° C. range. After 1 hour, 100 ml of 10% HCl aqueous solution was added to the bottle to quench the reaction and the resulted mixture was stirred for two hours. The organic layer was then isolated and further washed twice with 150 ml of deionized water. Toluene solvent was subsequently removed from the organic layer on a rota-evaporator. Analysis of the product mixture by high temperature simulated distillation (ASTM D2887, Modified) indicated oligomers yield was 96%. The oligomer mixture contained about 43% dimer, 24% trimer, 11% tetramer, 5% pentamer and 17% higher oligomers (FIG. 1).

Figure 2:
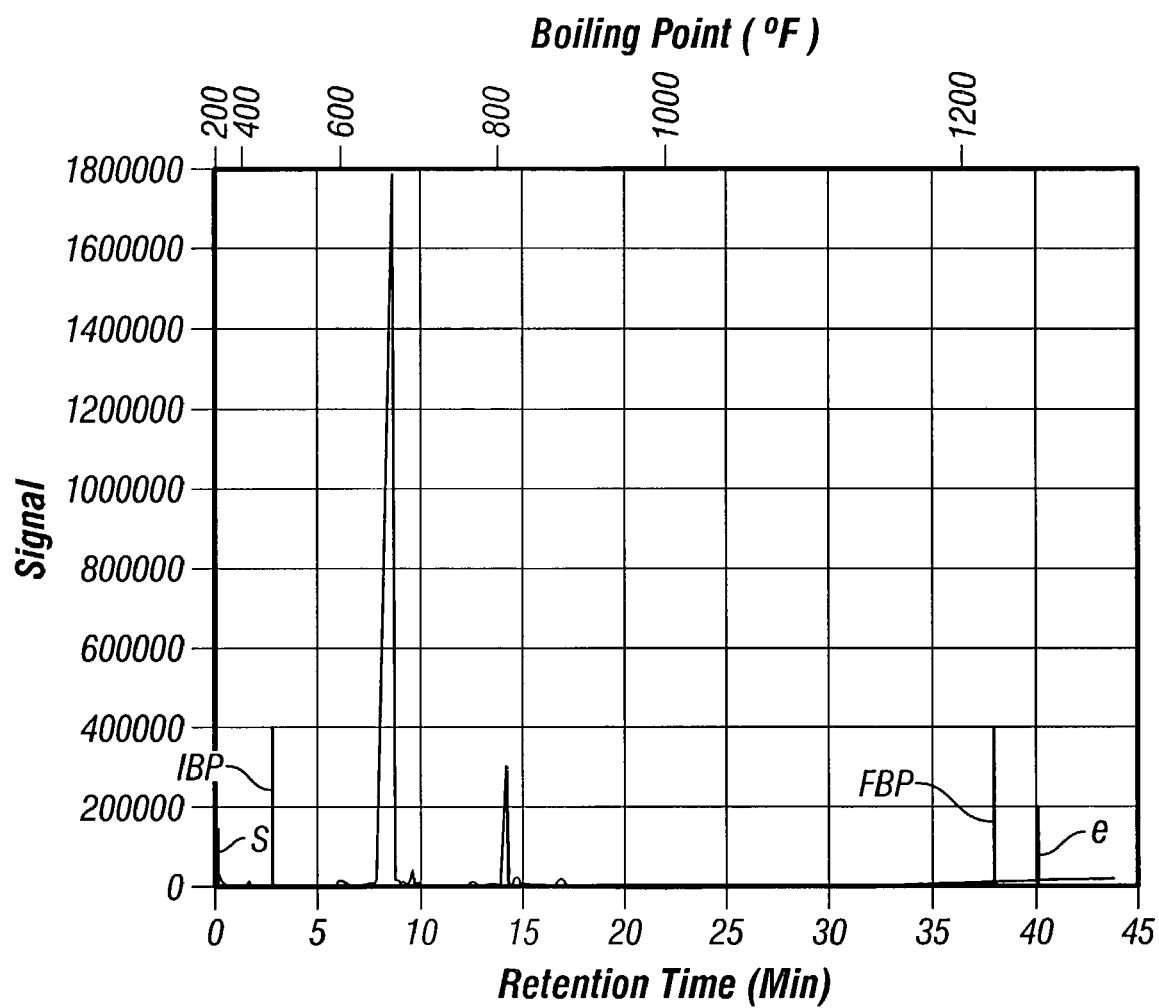
FIG. 2 shows a high temperature simulated distillation chromatogram for fraction E8-1 described in Example 8 containing 89% dimer, 7% trimer, and 4% higher oligomers.
Figure 3:
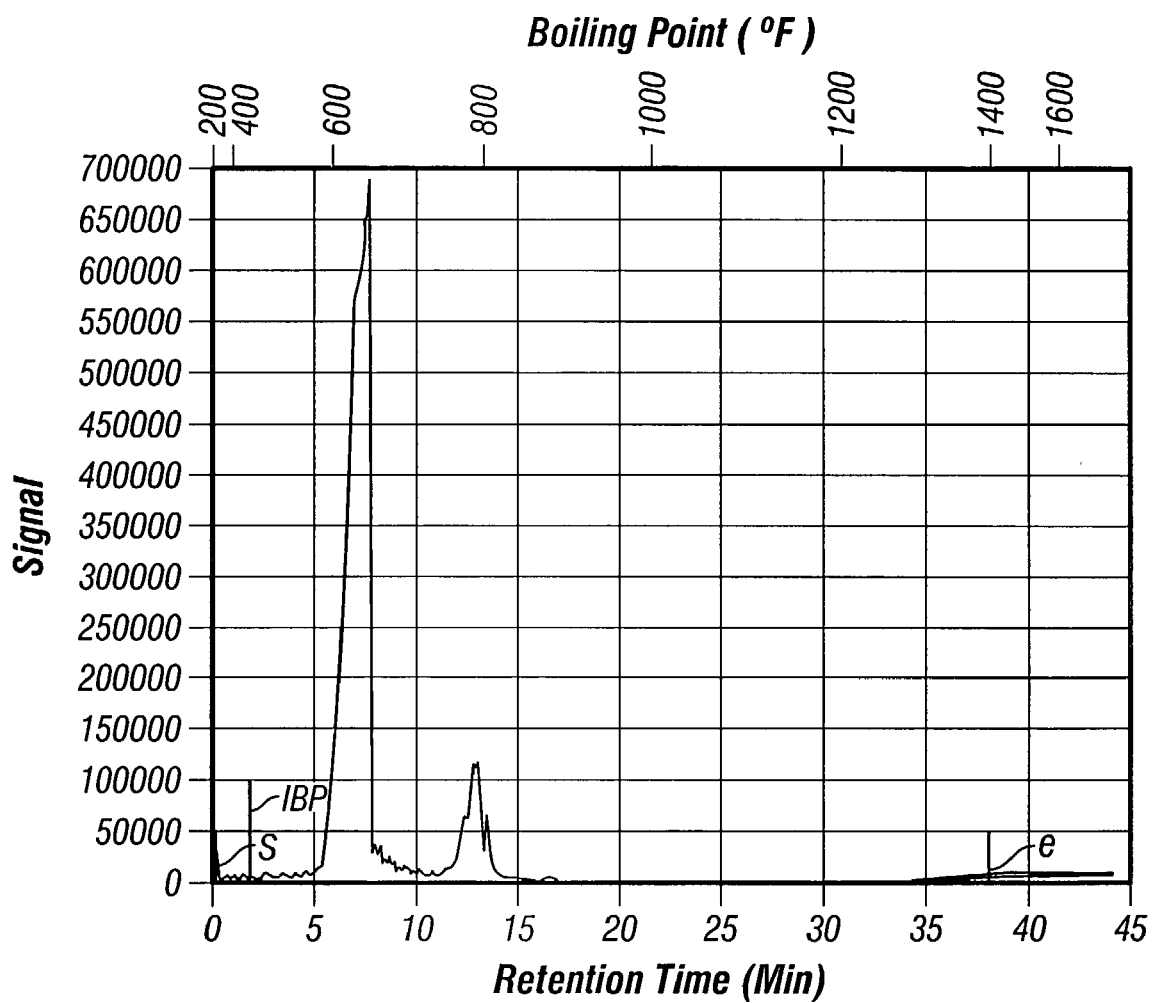
FIG. 3 shows a high temperature simulated distillation chromatogram for a commercial polyalphaolefin (Durasyn 162).

The oligomer mixture was hydrogenated and then fractionated by vacuum distillation. A fraction (Fraction E8-I) containing 89% dimer, 7% trimer, and 4% higher oligomers was collected and further characterized (FIG. 2). The viscosity properties of this fraction were determined to be kinematic viscosity at 100° C. (KV100) of 1.8 cSt, kinematic viscosity at 40° C. (KV40) of 5.3 cSt and viscosity index (VI) of 138.9. The PDSC induction time was recorded to be 44.2 minutes. In comparison, a commercial poly-alpha olefin obtained from British Petroleum (BP) under the trade name of Durasyn 162 with KV100 of 1.8 cSt, KV40 of 5.7 cSt and VI of 94.1 was measured to have PDSC induction time of 27.3 minutes. Durasyn 162 was determined to contain 85% dimer and 15% trimer (FIG. 3). Both the higher VI and longer PDSC induction time (better oxidation stability) of the newly synthesized poly-alpha olefin indicates it has substantially higher linearity than the existing commercial poly-alpha olefin product of equivalent viscosity.

EXAMPLE 9

Another fraction (Fraction E8-II) of the oligomer mixture synthesized in Example 8 contains 86% trimer, 10% tetramer, and 4% higher oligomers. It was measured to have KV100 of 3.6 cSt, KV40 of 14.8 cSt, VI of 129.7 and PDSC induction time of 31.4 minutes. In comparison, another commercial poly-alpha olefin obtained from BP under the trade name of Durasyn 164 with KV100 of 4.0 cSt, KV40 of 17.6 cSt and VI of 126 was measured to have a PDSC induction time of 27.4 minutes.

EXAMPLE 10

A 1000 ml pressure reaction bottle with a magnetic stir bar was thoroughly vacuumed followed by purging with argon. Then the bottle was charged with 100 ml of dried toluene (distilled over potassium) and 150 ml of 1-tetradecene (dried over 5A molecular sieves). At 70° C., 15 ml of 3.3 M methylaluminoxane in toluene solution was added to the reaction bottle and stirred for 20 minutes. Then 8 ml of 0.051 M bis(cyclopentadienyl)zirconium dichloride in toluene solution was injected into the bottle to start the reaction. Temperature of the reaction system was controlled by a constant temperature bath within ±1° C. range. After 1 hour, 300 ml of 10% HCl aqueous solution was added to the bottle to quench the reaction and the resulted mixture was stirred for two hours. The organic layer was then isolated and further washed twice with 300 ml of deionized water. Toluene solvent was subsequently removed from the organic layer on a rota-evaporator. Analysis of the product mixture by high temperature simulated distillation (ASTM D2887, Modified) indicated oligomers yield was 86%. The oligomer mixture contained about 85% dimer, 10% trimer, 3% tetramer, and 1% higher oligomers.

The oligomer mixture was hydrogenated and then fractionated by vacuum distillation. A fraction (Fraction E10-I) containing 45% dimer, 42% trimer, 10% tetramer and 3% higher oligomers was collected and further characterized. The viscosity properties of this fraction were determined to be KV100 of 5.1 cSt, KV40 of 21.8 cSt and VI of 175. The PDSC induction time was recorded to be 44.6 minutes. In comparison, another commercial poly-alpha olefin obtained from BP under the trade name of Durasyn 166 with KV100 of 5.9 cSt, KV40 of 31.0 cSt and VI of 135 was measured to have a PDSC induction time of 26.4 minutes.

EXAMPLE 11

Another fraction (Fraction E10-II) of the oligomer mixture synthesized in Example 10 contains mostly dimer and is a wax at ambient temperature. It was measured to have PDSC induction time of 48.4 minutes.

EXAMPLE 12

A third fraction (Fraction E10-III) of the oligomer mixture synthesized in Example 10 contains 16% dimer, 55% trimer, 13% tetramer and 16% higher oligomer. It was measured to have KV100 of 6.4 cSt, KV40 of 30.3 cSt, VI of 169 and PDSC induction time of 46.2 minutes.

EXAMPLE 13

The procedure was essentially the same as Example 10, except the reaction was run at 50° C. and 8 ml of 0.034 M bis(isopropylcyclopentadienyl)zirconium dichloride in toluene solution was used. The oligomers yield was 88%. The oligomers contained about 35% dimer, 22% trimer, 12% tetramer, and 31% higher oligomers.

The oligomer mixture was hydrogenated and then fractionated by vacuum distillation. A fraction (Fraction E13-I) containing 2% dimer, 40% trimer, 22% tetramer and 36% higher oligomers was collected and further characterized. It was measured to have KV100 of 9.2 cSt, KV40 of 50.3 cSt, VI of 166 and PDSC induction time of 34.7 minutes.

As demonstrated above, PAOs made in accordance with an embodiment of the invention may have one or more of the following characteristics: 1) substantial absence of tertiary hydrogen resulting from isomerization; 2) greater oxidative stability; 3) greater biodegradability; and 4) cost effectiveness. Therefore, lubricants made in accordance with an embodiment of the invention can be produced for relatively lower cost, have greater oxidation stability, and are environmentally safe. Other characteristics and advantages provided by embodiments of the invention are apparent to those skilled in the art.

In addition to their use as base oils and lubricant components, the products of the invention are also useful in applications such as air care, skin care, hair care, cosmetics, household products, cleaners, polishes, fabric care, textile coatings and textile lubricants, automotive products, car cleaners and polishes, fuel additives, oil additives, candles, pharmaceuticals, suspending agents, sun care, insecticides, gels, hydraulic fluids, transmission fluids, modifier for polymers, biodegradable applications and 2-cycle oils.

Although the invention has been described with respect to a number of limited embodiments, variations and modifications exist. The various components and method of use may be used in embodiments of the invention with or without modifications. The appended claims intend to cover such variations and modifications that fall within the scope of the invention as described herein.

What is claimed is:

1. A hydrogenated poly-alpha-olefin composition, comprising:
    one or more hydrogenated oligomers of an alpha-olefin, the oligomers having a molecular weight of about 10,000 or less and characterized by a substantially regio-regular structure, 14% by weight or greater of trimer, tetramer and higher oligomers, and being substantially free of tertiary hydrogen resulting from isomerization, said alpha olefin is represented by the formula $CH_2=CHR$ wherein R is a hydrocarbyl group.

2. The composition of claim 1, wherein the molecular weight of the oligomer is about 9,000 or less.

3. The composition of claim 1, wherein the molecular weight of the oligomer is about 7,000 or less.

4. The composition of claim 1, wherein the molecular weight of the oligomer is about 5,000 or less.

5. The composition of claim 1, wherein the molecular weight of the oligomer is about 3,000 or less.

6. The composition of claim 1, wherein the one or more oligomers are polymerized in the presence of a single site catalyst.

7. The composition of claim 6, wherein the single-site catalyst is a metallocene catalyst.

8. The composition of claim 6, wherein the single site catalyst comprises bis(cyclopentadienyl)zirconium dichloride.

9. The composition of claim 1, wherein the alpha olefin is 1-propene, 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene or 1-eicosene.

10. The composition of claim 1, wherein the oligomer is completely free of tertiary hydrogen due to isomerization.

11. The composition of claim 1, wherein the oligomer is a dimer, a trimer, a tetramer, a pentamer, a higher oligomer, or a mixture thereof.

12. The composition of claim 1, wherein the oligomer is fully saturated.

13. A lubricant comprising the poly-alpha-olefin composition of claim 1.

14. A method of making a hydrogenated non-isomerized oligomer comprising:
    contacting an olefin monomer in the presence of a single site catalyst, said olefin monomer is represented by the formula $CH_2=CHR$ wherein R is a hydrocarbyl group;
    effecting oligomerization of the olefin monomer to produce a substantially regio-regular oligomer having a molecular weight of about 10,000 or less and 14% by weight or greater of trimer, tetramer and higher oligomers;
    contacting the oligomer with hydrogen under hydrogenation conditions to produce a hydrogenated non-isomerized oligomer;
    and recovering the hydrogenated non-isomerized oligomer.

15. The method of claim 14 wherein the molecular weight of the oligomer is about 9,000 or less.

16. The method of claim 14 wherein the molecular weight of the oligomer is about 7,000 or less.

17. The method of claim 14 wherein the molecular weight of the oligomer is about 5,000 or less.

18. The method of claim 14, wherein the molecular weight of the oligomer is about 3,000 or less.

19. The method of claim 14, wherein the single-site catalyst is a metallocene catalyst.

20. The method of claim 14, wherein the single site catalyst comprises bis(cyclopentadienyl)zirconium dichloride.

21. The method of claim 14, wherein the olefin monomer is selected from the group consisting of aliphatic olefins, aromatic olefins, and cyclic olefins.

22. The method of claim 21, wherein the olefin monomer is an alpha olefin.

23. The method of claim 22, wherein the alpha olefin is 1-propene, 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene or 1-eicosene.

24. The method of claim 14 wherein the oligomer is substantially free of tertiary hydrogen due to isomerization.

25. The method of claim 24 wherein the oligomer is completely free of tertiary hydrogen due to isomerization.

26. The method of claim 14 wherein the reaction product is a mixture of oligomers.

27. The method of claim 26, wherein the mixture of oligomers are selected from a group consisting of dimer, trimer, tetramer, pentamer, and higher oligomers.

28. The method of claim 14, wherein the non-isomerized oligomer is used as one component of a lubricant.

29. The method of claim 28, wherein the lubricant comprises one or more lubricant additives.

30. The method of 14, wherein the oligomerzation yield is 66% by weight or greater.

31. The composition of claim 1 wherein 78% or less of the oligomers are dimers.

32. A lubricant comprising the poly-alpha-olefin composition of claim 31.

* * * * *